United States Patent [19]

Ryckman

[11] Patent Number: 5,734,061

[45] Date of Patent: Mar. 31, 1998

[54] PROCESS FOR PREPARING SPIROCYCLIC LACTAMS

[75] Inventor: David Ryckman, San Diego, Calif.

[73] Assignee: SmithKline Beecham Corporation, Philadelphia, Pa.

[21] Appl. No.: 656,334

[22] PCT Filed: Dec. 7, 1994

[86] PCT No.: PCT/US94/14083

§ 371 Date: Jun. 13, 1996

§ 102(e) Date: Jun. 13, 1996

[87] PCT Pub. No.: WO95/16657

PCT Pub. Date: Jun. 22, 1995

[51] Int. Cl.$^6$ .................................................. C07D 209/96
[52] U.S. Cl. ........................ 548/408; 546/208; 548/550; 540/350; 540/480; 540/602; 570/181; 570/186
[58] Field of Search ............................. 548/408, 550; 520/181, 186; 540/480, 602; 546/208

[56] References Cited

U.S. PATENT DOCUMENTS 4,963,557 10/1990 Badger et al. .......................... 514/278
5,049,680 9/1991 O'Lenick et al. ........................ 548/550

OTHER PUBLICATIONS

Bailey et al. "J. Org. Chem." vol. 49, pp. 2048–2107 (1948).
Tetrahydron Letters, vol. 23, No. 49, pp. 5123–5125 (1982).
Tetrahydron Letters, vol. 30, No. 34, pp. 4531–4534 (1989).
J. Chem. Soc., Chem. Commun, pp. 518–519 (1985).

*Primary Examiner*—Robert T. Bond
*Attorney, Agent, or Firm*—Cushman Darby & Cushman IP Group Pillsbury Madison & Sutro LLP

[57] ABSTRACT

The invention is directed to an improved process for the preparation of spirocyclic lactams which utilizes diiodides in the spiro alkylation of lactams N-substituted with a tertiary amine group. The resultant spirocyclic lactams are useful in the production of various substituted azaspiranes which are useful as immunomodulatory agents.

14 Claims, No Drawings

PROCESS FOR PREPARING SPIROCYCLIC LACTAMS

This case is a 371 of PCT/US 94/14083, filed 7 Dec. 1994 which claims priority of British Application 9325854.9, filed 17 Dec. 1993.

The present invention relays to an improved process for the preparation of spirocyclic lactams which utilizes α,ω-diiodides in the spiro alkylation of lactams N-substituted with a tertiary amine group. The resultant spirocyclic lactams are useful in the production of various substituted azaspiranes. Such compounds are described in U.S. Pat. No. 4,963,557 as being useful as immunomodulatory agents.

BACKGROUND OF THE INVENTION

Processes for the preparation of spirocyclic lactams have previously been described. In particular radical cyclizations are reported in (a) Nagushima, H. et al., *J.C.S. Chem. Commun.*, 1985, 518, (b) Jolly, R. S. et al., *J. Am. Chem. Soc.*, 1988, 110, 7536 and (c) Cossy, J. et al., *Tetrahedron Lett.*, 1989, 4531. None of the above references, however, describe the preparation of spirocyclic lactams N-substituted with a tertiary amine substituent.

Additionally, U.S. Pat. No. 4,963,557 describes the formation of cyclic-1-carboxy-1-acetic acid anhydrides via the dehydration of cyclic-1-carboxy-1-acetic acid compounds. As used therein subsequent amidation of the anhydride followed by reduction of the spiroimides thus obtained yields pharmaceutically active azaspiranes N-substituted with a tertiary amine substituent.

The above disclosures require numerous reaction steps and difficult isolation procedures resulting in low overall yields. Thus, there is a need in the art for a safe, economical and reliable method to prepare spirocyclic lactams N-substituted with a tertiary amine substituent.

This invention relates to the novel use of α,ω-diiodides as difunctional electrophiles in the spiroalkylation of lactams N-substituted with a tertiary amine group. The invented process is advantageous in that it shortens the number of overall steps, utilizes a convergent synthetic scheme, eliminates the need for chromatography and increases overall yield.

This discovery is particularly surprising in view of corresponding research which concluded that chlorides, bromides, tosylates and mesylates fail when substituted for iodine in the invented process.

SUMMARY OF THE INVENTION

This invention relates to an improved process for the preparation of spirocyclic lactams which utilizes α,ω-diiodides in the spiroalkylation of lactams N-substituted with a tertiary amine group.

This invention relates to an improved process for the preparation of 2-azaspiro [4.5]decane ring systems.

This invention specifically relates to an improved process for the preparation of
N,N-dimethyl-8,8-dipropyl-2-azaspiro [4.5]decane-2-propanamine;
N,N-diethyl-8,8-dipropyl-2-azaspiro [4.5]decane-2-propanamine; and
2-(3-piperidinopropyl)-8,8-dipropyl-2-azaspiro [4.5]decane.

DETAILED DESCRIPTION OF THE INVENTION

As used herein, the term N,N-dimethyl-8,8-dipropyl-2-azaspiro[4.5]decane-2-propanamine refers to a compound of Formula I where n is 3, $R^3$ and $R^4$ are each methyl and $R^1$ and $R^2$ are each propyl.

As used herein, the term N,N-diethyl-8,8-dipropyl-2-azaspiro [4.5]decane-2-propanamine refers to a compound of Formula I where n is 3, $R^3$ and $R^4$ are —$CH_2$—$CH_3$ and $R^1$ and $R^2$ are each propyl.

As used herein, the term 2-(3-piperidinopropyl)-8,8-dipropyl-2-azaspiro [4.5]decane refers to a compound of Formula I where n is 3, $R^3$ and $R^4$ are joined together to form a cyclic alkyl group containing 5 carbon atoms and $R^1$ and $R^2$ are each propyl.

By the term "appropriate solvent" as used herein is meant a solvent such as tetrahydrofuran, hexane, or diethyl ether.

By the term "organic solvent" as used herein is meant a solvent such as methylene chloride, ethylene chloride, chloroform, ethylene glycol, carbon tetrachloride, tetrahydrofuran (THF), ethyl ether, toluene, ethyl acetate, hexane, dimethylsulfoxide (DMSO), N,N'-dimethyl-N,N'-propylene urea, N-methyl-2-pyrrolidinone, methanol, isopropyl alcohol, dimethylformamide (DMF), pyridine, quinoline or ethanol.

By the term "reduced temperature" as used herein is meant below 25° C., preferably at 0° C. when a salt of hexamethyldisilane (as described herein) is used, preferably at –78° C. when an alkyllithium reagent (as described herein) is used.

By the term "appropriate reducing agent" as used herein is meant a compound capable of reductively removing an oxo substituent, such as lithium aluminum hydride or, preferably, $NaBH_4/BF_3.Et_2O$.

By the term "active base" as used herein is meant (i) an alkyllithium reagent; preferably, n-butyllithium, sec-butyllithium or tert-butyllithium in conjunction with an appropriate alkylamine base, preferably diisopropylamine or (ii) salts of hexamethyldisilane, such as sodium-, lithium- or, preferably, potassium-hexamethyldisilylazide.

Pharmaceutically acceptable salts, hydrates and solvates of Formula (I) compounds are formed where appropriate by methods well known to those of skill in the art.

The present invention provides a process for the preparation of a compound of Formula (I).

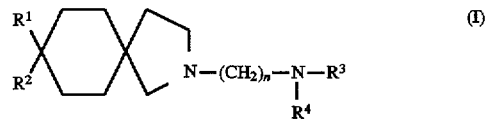

in which:

n is 1–7

$R^1$ and $R^2$ are the same or different and are selected from straight chain, branched chain or cyclic alkyl, provided that the total number of carbon atoms contained by $R^1$ and $R^2$ when taken together is 4–10; or $R^1$ and $R^2$ are joined together to form a cyclic alkyl group containing 3–7 carbon atoms;

$R^3$ and $R^4$ are the same or different straight chain alkyl groups of 1–3 carbons; or $R^3$ and $R^4$ are joined together to form a cyclic alkyl group containing 4–7 carbon atoms;

or a pharmaceutically acceptable salt, hydrate or solvate thereof, which comprises:

a) reacting, in an appropriate solvent and at a reduced temperature, a compound of Formula (II)

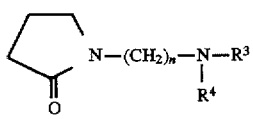 (II)

wherein n, $R^3$ and $R^4$ are as defined above, in the presence of an active base with a compound of the Formula (III)

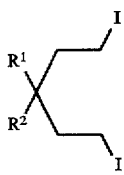 (III)

wherein $R^1$ and $R^2$ are as defined above to form a compound of Formula (IV)

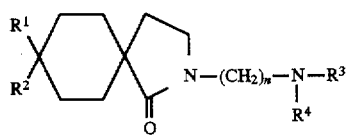 (IV)

wherein n, $R^1$, $R^2$, $R^3$ and $R^4$ are as defined above and b) subsequently, in an appropriate solvent and in the presence of an appropriate reducing agent, reducing the oxo substituent to form a compound of Formula I and thereafter optionally forming a pharmaceutically acceptable salt, hydrate or solvate thereof.

Preferably, therefore, the process of the present invention is particularly useful for preparing a compound of structure (IVA)

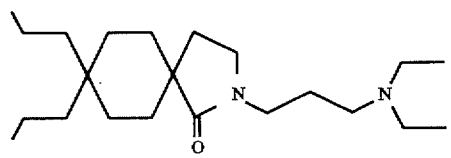 (IVA)

and converting the same into the following compound of structure (IA)

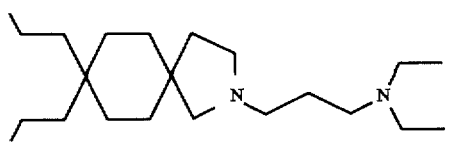 (IA)

or a pharmaceutically acceptable salt, hydrate or solvate thereof.

Preferably, therefore, the process of the present invention is particularly useful for preparing a compound of structure (IVB)

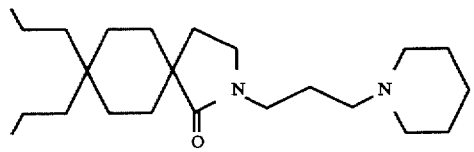 (IVB)

and converting the same into the following compound of structure (IB)

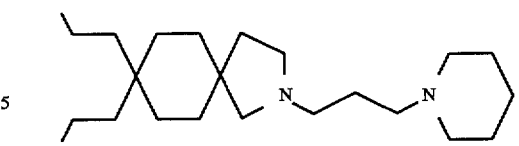 (IB)

or a pharmaceutically acceptable salt, hydrate or solvate thereof.

Preferably, therefore, the process of the present invention is particularly useful for preparing a compound of structure (IVC)

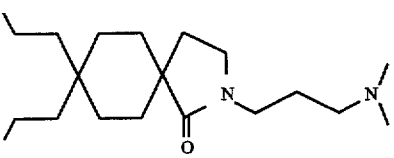 (IVC)

and converting the same into the following compound of structure (IC)

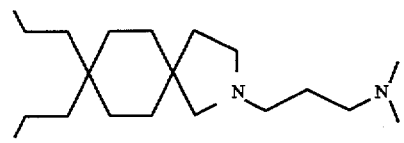 (IC)

or a pharmaceutically acceptable salt, hydrate or solvate thereof.

Also, prepared in utilizing the presently invented process are novel intermediates of Formula (III)

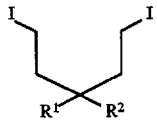 III wherein $R^1$ and $R^2$ are as defined in Formula I.

Novel intermediates of Formula (III) of the present invention can be prepared by methods outlined in Schemes 1–3 below and in the Examples from known and readily available ethyl cyanoacetate

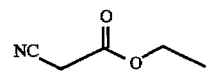

and from known and readily available cyanoacetamide

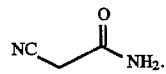

Scheme I

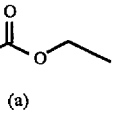 (a)  $\xrightarrow{CH_3CO_2H, NH_4OAc}$  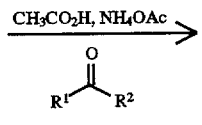

(z)

Scheme I

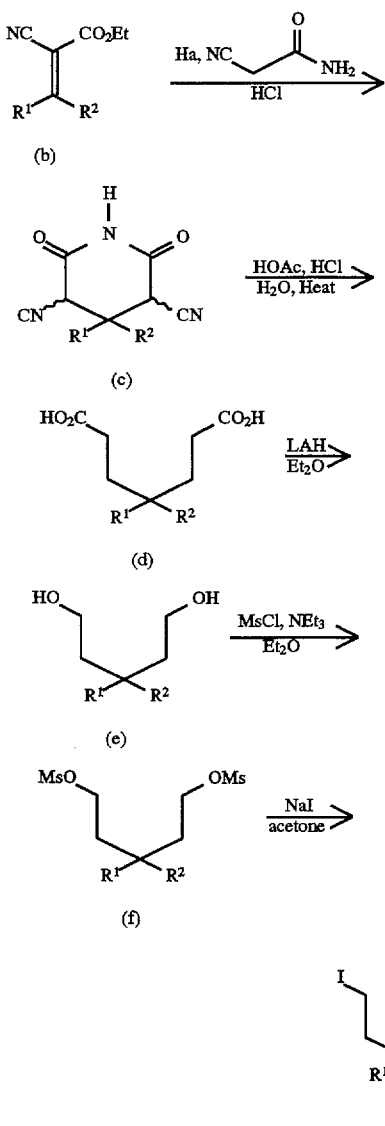

Scheme I outlines formation of novel intermediates of Formula (III). As used in Scheme I compounds of Formula (b) are prepared by reacting compound (a) a compound of formula (z), acetic acid and NH$_4$OAc in cyclohexane at reflux with constant water removal.

A compound of Formula (b), sodium and cyanoacetamide are reacted in absolute ethanol, followed by the addition of concentrated HCl to yield compounds of Formula (c).

Acidification of compounds (c) yields compounds (d) which are subsequently reduced to yield compounds (e).

Compounds (e) are reacted with mesyl chloride and triethylamine preferably in diethyl ether, preferably at 0° C. to yield compounds of Formula (f).

Reaction of compounds (f) with NaI, preferably in acetone, preferably at room temperature yields compounds of Formula (g).

As used in Scheme I, compounds of Formula (z) are known and readily available or can be prepared from known and readily available materials by methods well known to those of skill in the art.

Scheme II

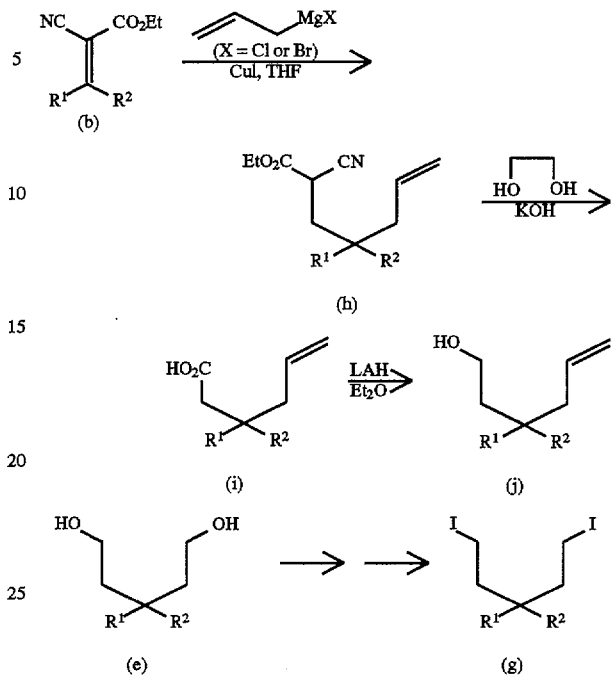

Scheme II outlines formation of novel intermediates of Formula (III). The starting material in Scheme II are formula (b) compounds prepared as described in Scheme I.

As used in Scheme II, formula (b) compounds are treated with an allyl Grignard reagent, preferably allyl magnesium chloride, in an appropriate solvent, preferably tetrahydrofuran or diethyl ether, preferably at reflux temperature to yield formula (h) compounds. Alternatively, a halogen copper reagent, preferably copper iodide, is added to the allyl Grignard reagent in tetrahydrofuran, preferably at −78° C., to form an allyl copper halo reagent. Said allyl copper reagent is reacted with a formula (b) compound, preferably at 0° C. to yield formula (h) compounds.

Formula (h) compounds and a base, preferably potassium hydroxide, in an organic solvent, preferably ethylene glycol is reacted, preferably at reflux to yield formula (i) compounds.

Formula (i) compounds are reduced, preferably with lithium aluminum hydride, in an organic solvent, preferably diethyl ether, to yield formula (j) compounds.

Formula (j) compounds in an organic solvent, preferably methanol, preferably at −78° C. are reacted with methylsulfide in the presence of ozone, followed by the addition of a base, preferably sodium borohydride, preferably at 0° C. to yield Formula (e) compounds.

Formula (e) compounds are reacted as in Scheme I to yield Formula (g) compounds in two steps.

Scheme III

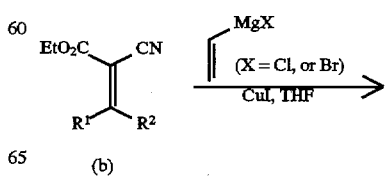

-continued
Scheme III

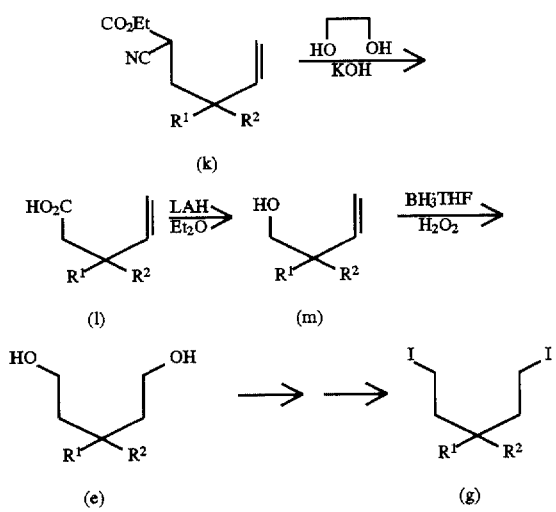

Scheme III outlines formation of novel intermediates of Formula (III). The starting materials in Scheme III are Formula (b) compounds prepared as described in Scheme I.

As used in Scheme III, compounds of Formula (b) are treated with a Grignard reagent, preferably vinyl magnesium bromide, in an appropriate solvent, preferably tetrahydrofuran or diethyl ether, preferably at reflux temperature to yield compounds of Formula (k). Alternatively, a halogen copper reagent, preferably copper iodide, in tetrahydofuran is added to the Grignard reagent, preferably at −78° C., to form a vinyl copper halo reagent. Said vinyl copper halo reagent is reacted with compounds (b), preferably at 0° C. to yield compounds (k).

Compounds (k) and a base, preferably potassium hydroxide, in an organic solvent, preferably ethylene glycol, are reacted preferably at reflux to yield compounds (l).

Compounds (l) are reduced, preferably with lithium aluminum hydride, in an organic solvent, preferably diethyl ether, to yield compounds (m).

Compounds (m) in an organic solvent preferably tetrahydrofuran, at −78° C. are reacted with $BH_3$, followed by $H_2O_2$ to yield compounds (e).

Compounds (e) are reacted as in Scheme I to yield compounds (g) in two steps.

Also, prepared in utilizing the presently invented process are novel intermediates of Formula II

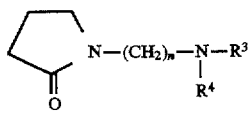

wherein n, $R^3$ and $R^4$ are as defined in Formula I.

Novel intermediates of Formula II of the present invention can be prepared by methods outlined in Scheme IV below and in the examples from known and readily available butyrolactone

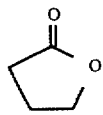

-continued
Scheme IV

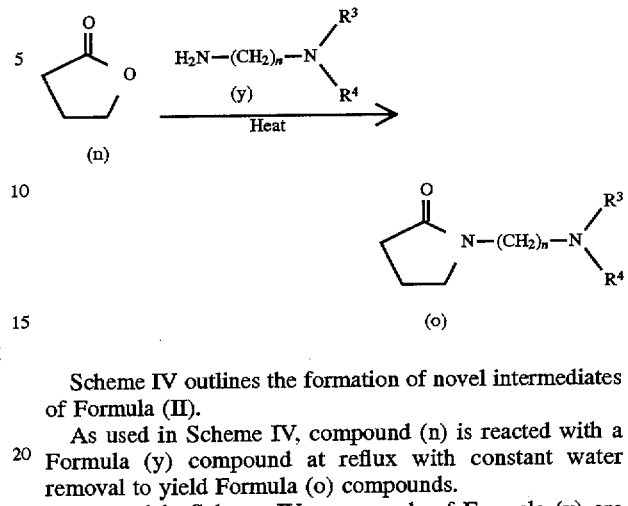

Scheme IV outlines the formation of novel intermediates of Formula (II).

As used in Scheme IV, compound (n) is reacted with a Formula (y) compound at reflux with constant water removal to yield Formula (o) compounds.

As used in Scheme IV compounds of Formula (y) are known and readily available or can be prepared from known and readily available materials by methods well known to those of skill in the art.

EXAMPLE 1

Corresponding to Scheme I 3,3-Dipropyl-1,5-diiodopentane (i) Ethyl α-cyano-α-(4-heptylidene)acetate In a 100 mL round-bottom flask was dissolved 4-heptanone (11.4 g, 0.10 mmole) and ethyl cyanoacetate (11.30 g, 0.100 mole) in cyclohexane (25 mL). Acetic acid (1.0 mL) and $NH_4OAc$ (2.0 g) were added. The solution was magnetically stirred and heated to reflux with a Dean-Stark trap in place overnight under $N_2$. The reaction was cooled to ambient, diluted with ethyl acetate (100 mL) washed with $H_2O$ (2×50 mL) and brine (25 mL). The organic extracts were dried ($Na_2SO_4$, filtered and concentrated under vacuum to give an oil that was distilled (bp. 135°–137° C., 20 mmHg) to give Ethyl α-cyano-α-(4-heptylidene)acetate (16.65 g, 0.080 mole, 80%). IR (neat film) 2950, 2910, 2860, 2200, 1725, 1570, 1235, 1085 cm$^{-1}$; $^1$H NMR (400 MHz, $CDCl_3$) δ 4.15 (q, J=9 Hz, 2H), 2.60 (t, J=10 Hz, 2H), 2.38 (t, J=10 Hz, 2H), 1.25 (t, J=9 Hz, 2H), 1.40 (sextet, J=9 Hz, 2H), 1.25 (t, J=9 Hz, 3H), 0.88 (m, 6H); $^{13}$C NMR (100 MHz, $CDCl_3$) δ 181.2, 161.5, 115.5, 104.6, 61.4, 40.2, 35.2, 21.9, 21.4, 14.1, 13.8 (one carbon not observed due to overlap); MS (CI) m/e 211 (14.5), 210 (100), 209 (3.59), 182 (3.5), 164 (2.8); HRMS (CI) calcd for $C_{12}H_{20}NO_2$ (M+H) m/e 210.1484, found 210.1491.

(ii) 3,5-Dicyano-4,4-dipropylcyclohexylimide

In a 100 mL round-bottom flask equipped with a drying tube and magnetic stir bar was added sodium (0.795 g, 34.6 mmole) to absolute ethanol (50 mL). To the room temperature solution was added cyanoacetamide (2.91 g, 34.6 mole) as a solid to give a white suspension. After 2–3 min, ethyl α-cyano-α-(4-heptylidene)acetate (7.22 g, 34.6 mole) was added rapidly and the mixture stirred at room temperature 2 h to give a clear solution. Water (50 mL) then concentrated HCl (8.75 mL) was added. After standing in the freezer overnight, the precipitate was collected by filtration, washed with ethanol and allowed to air dry to give 3,5-Dicyano-4,4-dipropylcyclohexylimide (7.40 g, 29.9 mole, 87%). mp. 218°–219° C. Mixture of two isomers by capillary GC.RT= 7.86 min, 51%, RT=7.94 min, 43%; IR (FTIR in KBr)

3600–3000, 3008, 1752, 1710, 1234 cm$^{-1}$; $^1$H NMR (400 MHz, CDCl$_3$) δ 8.38 (br, 1H); 3.81 (s, 2H), 1.8–1.3 (m, 6H), 1.09 (t, J=Hz, 2H), 0.90 (m, 6H); $^{13}$C NMR (100 MHz, d$^6$, DMSO) 165.3, 114.3, 43.3, 41.6, 38.8, 38.1, 17.0, 15.9, 14.5, 14.1; MS m/e (CI) 249 (16.5), 248 (70.8); Anal. Calcd for C$_{11}$H$_{17}$NO$_2$. ½ H$_2$O (256.306: C, 60.92; H, 7.08; N, 16.39. Found: C, 60.96; H, 6.84; N, 16.56.

(iii) 3,3-Dipropylpentandioic acid

In a 100 mL round-bottom flask equipped with a magnetic stir bar was dissolved 3,5-Dicyano-4,4-dipropylcyclohexylimide (350 mg, 1.42 mole) in glacial acetic acid (10 mL). Concentrated HCl (10 mL) and H$_2$O (10 mL) were added. The solution was refluxed 12 h then concentrated to 10 mL by simple distillation. The solution was extracted with CH$_2$Cl$_2$ (3×10 mL). The combined extracts were washed with H$_2$O and brine, dried (Na$_2$SO$_4$), filtered and concentrated. The residue was crystallized from 30% ethyl acetate-hexanes to give 3,3-Dipropylpentandioic acid (280 mg, 1.30 mmole, 91%). mp. 107° C., d; IR (KBr) 3500–2500, 3000–2800, 1726, 1698, 1303, 1207, 915 cm$^{-1}$; $^1$H NMR (400 MHz, d$^6$-DMSO) δ 11.9 (br s, 2H), 2.35 (s, 9H), 1.35 (m, 4H0, 1.20 (m, 4H), 1.20 (m, 4H), 0.79 (t, J=9 Hz, 6H); $^{13}$C NMR (100 MHz, d$^6$-DMSO) δ 173.0, 40.2, 38.8, 37.1, 15.9, 14.7; MS 9e intensity) 217 (M$^+$, 3), 216 (0.5), 200 (13), 199 (100), 198 (28), 157 (2); Anal. Calcd for C$_{11}$H$_{20}$O$_4$: C, 61.09; H, 9.32. Found: C, 61.10; H, 9.16.

(iv) 3,3-Dipropyl-1,5-diiodopentane 3,3-Dipropylpentandioic acid was converted to the corresponding diol, in quantitative yield, by reaction with lithium aluminum hydride in diethyl ether.

In a 500 mL round-bottom flask equipped with a magnetic stir bar was dissolved the diol (6.40 g, 34.04 mmole) in ether (150 mL). The solution was cooled to 0° C. and triethylamine (14.18 g, 140.16 mmole) followed by mesyl chloride (9.75 g, 85.1 mmole) were added. The reaction was stirred 5 min then quenched with saturated NaHCO$_3$ (100 mL) and diluted with ether (100 mL). The organic layer was washed with H$_2$O (100 mL) and brine (2×50 mL), dried (Na$_2$SO$_4$) filtered, and concentrated to yield the dimesylate as an oil (11.53 g, 33.5 mmole, 98.4%). R$_f$(silica gel, 1:1 hexane-:ethyl acetate)=0.82.

The dimesylate was immediately dissolved in acetone (500 mL) and stirred under N$_2$ in a 1 L round-bottom flask as NaI (102 g, 680 mmole) was added as a solid. After stirring for 5 days in the dark at room temperature, the reaction was diluted with ether (100 mL) and washed with saturated NH$_4$Cl, 25% Na$_2$S$_2$O$_8$ and brine. The organic layer was dried (Na$_2$SO$_4$), filtered, and concentrated to a white solid. The residue was filtered through silica gel eluting with 10% ethyl acetate-hexane to give, after concentration, 3,3-dipropropyl-1,5-diiodopentane (12.60 g, 30.88 mmole, 91% for the two steps). mp 60°–62° C. IR (FTIR in KBr) 3000–2800, 1451, 1465, 1178, 1195, 600, 300 cm$^{-1}$; $^1$H NMR (400 MHz, CDCl$_3$) δ 3.19 (m, 4H), 1.9 (m, 4H), 1.30 (m, 8H), 0.95 (t, J=10 Hz, 6H); $^{13}$C NMR (100 MHz, CDCl$_3$ δ 43.7, 41.8, 38.1, 16.2, 14.8, 0.2; MS m/e (CI) 408 (1.14), 282 (11.47), 281 (100), 253 (2.3), 233 (2.1), 225 (5.73), 211 (6.0), 185 (9.7), 169 (24.5), 153 (6.7); Anal. Calcd for C$_{11}$H$_{22}$I$_2$: C, 32.37; H, 5.43; I, 62.19. Found: C, 32.60; H, 5.43; I, 61.85.

EXAMPLE 2

Corresponding to Scheme IV N-(Dimethylaminopropyl) butyrolactam

Butyrolactone (86.09 g, 1.00 mole) and N,N-Dimethylaminopropylamine (102.18 g, 1.00 mole) were combined in a 500 mL round-bottom flask equipped with a magnetic stir bar and Dean-Stark trap. The mixture was heated at reflux. After 1 eq. of H$_2$O was collected (8–10 h) the reaction was cooled to room temperature. The Dean-Stark trap was replaced with a fractionating column and the product was distilled under vacuum to yield to N-(Dimethylaminopropyl) butyrolactam (145 g, 0.85 mole, 85%). bp 79°–84° C., 0.25 mmHG; IR (neat film) 2920, 2750, 1780, 1650, 1450, 1430, 1260, 1280 cm$^{-1}$; $^1$H NMR (400 MHz, CDCl$_3$) δ 3.15 (m, 2H), 3.05 (m, 2H), 2.07 (m, 2H), 2.02 (m, 2H), 2.0 (s, 6H), 1.75 (m, 2H), 1.42 (m, 2H); $^{13}$C NMR (100 MHz, CDCl$^3$) δ 174.2, 56.5, 46.7, 45.0 (double intensity), 40.1, 30.5, 25.1, 17.4; MS m/e (CI) 172 (17.2), 171 (100), 170 (5.3), 169 (11.9), 127 (1.3), 126 (15.5); HRMS (CI) calcd for C$_9$H$_{19}$N$_2$O (MH) m/e 171.1497, found 171.1503; Anal Calcd for C$_9$H$_{18}$N$_2$O: C, 63.49; H, 10.66; N, 16.45. Found: C, 63.12; H, 10.68; N, 16.17.

EXAMPLE 3

N-(3-(Dimethylamino)propyl)-8,8-dipropyl-2-azaspiro [4.5]decane (i) N-(3-(Dimethylamino)propyl)-8,8-dipropyl-2-azaspiro [4.5]decane-1-one In a dry 250 mL round-bottom flask under N$_2$ was dissolved diisopropylamine (5.06 g, 50.0 mmole) in THF (35 mL). The solution was cooled to −25° C. With magnetic stirring, n-BuLi (2.5M, 20 mL, 50 mmole) was added over 10 min. After stirring an additional 30 min., the solution was cooled to −78° C. N-(Dimethylaminopropyl)butrolactam (3.40 g. 20.0 mmole) was added via syringe as a THF (5 ml) solution over 10 min. The solution was stirred an additional 1.5 h. 3,3-Dipropyl-1,5-diiodopentane was added as a THF (5 mL) solution over 10 min. The reaction was stirred 4 h at −78° C. then warmed to room temperature and allowed to stir 48 h. Saturated NH$_4$Cl (20 mL) was added and the mixture concentrated under reduced pressure. The residue was diluted with CH$_2$Cl$_2$ (100 mL). The organic layer was washed with H$_2$O (2×25 mL) then dried (K$_2$CO$_3$), filtered and concentrated at reduced pressure. The oil was dissolved in ether (200 mL) and treated with 6N HCl (200 mL). The aqueous layer was washed with ether (2×75 mL), basified with 50% NaOH (with cooling in an ice bath) and extracted with ether (3×50 mL). The organic extracts were washed with brine, dried (K$_2$CO$_3$) filtered, and concentrated. The resultant oil was filtered through silica gel eluting with 15% Net$_3$-EtOAc to remove some base line impurities to give N-(3-(Dimethylamino)propyl)-8,8-dipropyl-2-azaprio[4.5] decane-1-one (3.75 g, 18.4 mmole, 92%). IR (neat film) 2950, 2920, 2860, 1735, 1685, 1450, 1260, 1240 cm$^{-1}$; $^1$H NMR (400 MHz, CDCl$_3$) δ 3.25 (m, 4H), 2.25 (m, 2H), 2.20 (s, 6H), 1.82 t, J=6 Hz, 2H), 1.79 (m, 2H), 1.63 (m, 2H), 1.45 (br, 2H), 1.30 (m, 2H), 1.2–0.9 (m, 10H), 0.87 (m, 6H); $^{13}$C NMR (100 MHz, CDCl$_3$) δ 179.2, 56.9, 45.4 (double intensity), 45.0, 44.8, 43.8, 38.4, 34.3, 34.0, 31.5 (double intensity), 29.5, 27.9 (double intensity), 25.5, 16.2, 16.0, 14.9, 14.8; MS m/e (CI) 325 (18.8), 324 (22.5), 323 (100), 322 (11.6), 321 (21.7), 307 (1.21), 279 (8.5); HRMS (CI) calcd for C$_{20}$H$_{39}$N$_2$O (M+H) m/e 323.3062, found 323.3050.

(ii) N-(3-(Dimethylamino)propyl)-8,8-dipropyl-2-azaprio[4.5]decane

In a 50 mL round-bottom flask lithium aluminum hydride (11.8 mg, 0.311 mmole) was suspended in ether (5 mL) by means of a magnetic stir bar. N-(3-(Dimethylamino)propyl) -8,8-dipropyl-2-azaprio[4,5]decane-1-one (100 mg, 0.311 mmole) was added as an ether (5 mL) solution over 15 min. The reaction was stirred an additional 30 min then quenched saturated $Na_2SO_4$, filtered and concentrated under reduced pressure to give N-(3-(Dimethylamino)propyl)-8,8-dipropyl-2-azasprio[4.5]decane as an oil (88 mg, 0.285 mmole, 92%).

EXAMPLE 4

N-(3-(Dimethylamino)propyl)-8,8-dipropyl-2-azaspiro[4.5]decane-1-one

In a dry 12 L flask under $N_2$ was dissolved potassium hexamethyldisilyazide (1139 g, 5.7 mole) in hexanes (2 L). The solution was cooled to 0° C. With stirring, a solution of N-(Dimethylaminopropyl)butrolactam (387.1 g, 2.28 mole) and 3,3-Dipropl-1,5-diiodopetane (845 g, 2.07 mole) in hexanes (2 L) was added over a period of 1.5 hours. The reaction was stirred over night at 0° C. Saturated $NH_4Cl$ (1.2 L) was added. The aqueous layer was separated and extracted with hexanes (2 L). The combined hexanes layers were washed with saturated NaCl (2 L), dried with $Na_2SO_4$ and concentrated to yield the title compound as a dark brown oil (71%, 1.62 moles).

Without further elaboration, it is believed that one skilled in the art can, using the preceding description, utilize the present invention to its fullest extent. The following Examples are, therefore, to be construed as merely illustrative and not a limitation of the scope of the present invention in any way.

What is claimed is:

1. A process for the preparation of a compound of Formula (I)

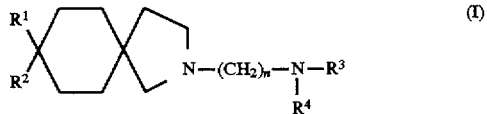

in which:

n is 1–7

$R^1$ and $R^2$ are the same or different and are selected from straight chain, branched chain or cyclic alkyl, provided that the total number of carbon atoms contained by $R^1$ and $R^2$ when taken together is 4–10; or $R^1$ and $R^2$ are joined together to form a cyclic alkyl group containing 3–7 carbon atoms;

$R^3$ and $R^4$ are the same or different straight chain alkyl groups of 1–3 carbons; or $R^3$ and $R^4$ are joined together to form a cyclic alkyl group containing 4–7 carbon atoms;

or a pharmaceutically acceptable salt, hydrate or solvate thereof, which comprises:

a) reacting, in an appropriate solvent and at a reduced temperature, a compound of Formula (II)

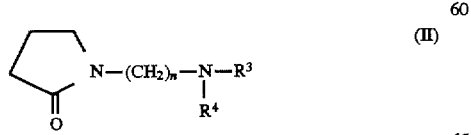

wherein n, $R^3$ and $R^4$ are as defined above, in the presence of an active base with a compound of the Formula (III)

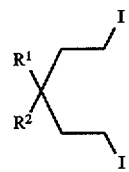

wherein $R^1$ and $R^2$ are as defined above to form a compound of Formula IV

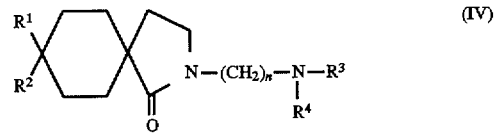

wherein n, $R^1$, $R^2$, $R^3$ and $R^4$ are as defined above and b) subsequently, in an organic solvent and in the presence of an appropriate reducing agent, reducing the oxo substituent to form a compound of Formula I, and thereafter optionally forming a pharmaceutically acceptable salt, hydrate or solvate thereof.

2. A process according to claim 1 in which the appropriate solvent is hexane, the reduced temperature is about 0° C., the active base is potassium hexamethyldisilyazide, the organic solvent is ether and the appropriate reducing agent is $NaBH_4/BF_3.Et_2O$.

3. A process according to claim 2 in which $R^1$ and $R^2$ are each propyl and n is 3.

4. A process according to claim 3 wherein the compound prepared is N,N-dimethyl-8,8-dipropyl-2-azaspiro[4.5]decane-2-propanamine; or a pharmaceutically acceptable salt, hydrate or solvate thereof.

5. A process according to claim 3 wherein the compound prepared is N,N-diethyl-8,8-dipropyl-2-azaspiro[4.5]decane-2-propan-3-amine; or a pharmaceutically acceptable salt, hydrate or solvate thereof.

6. A process according to claim 3 wherein the compound prepared is 2-(3-piperidinopropyl)-8,8-dipropyl-2-azaspiro[4.5]decane or a pharmaceutically acceptable salt, hydrate or solvate thereof.

7. A process for the preparation of a compound of Formula (IV).

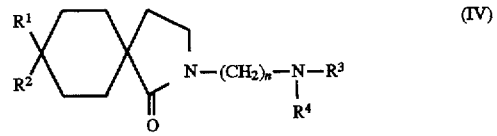

in which:

n is 1–7

$R^1$ and $R^2$ are the same or different and are selected from hydrogen or straight chain, branched chain or cyclic alkyl, provided that the total number of carbon atoms contained by $R^1$ and $R^2$ when taken together is 4–10; or $R^1$ and $R^2$ are joined together to form a cyclic alkyl group containing 3–7 carbon atoms;

$R^3$ and $R^4$ are the same or different straight chain alkyl groups of 1–3 carbons; or $R^3$ and $R^4$ are joined together to form a cyclic alkyl group containing 4–7 carbon atoms;

or a pharmaceutically acceptable salt, hydrate or solvate thereof, which comprises reacting, in an appropriate solvent and at a reduced temperature, a compound of Formula (II)

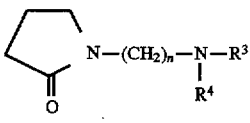 (II)

wherein n, R³ and R⁴ are as defined above, in the presence of an active base with a compound of the Formula (III)

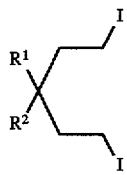 (III)

wherein R¹ and R² are as defined above.

8. A process according to claim 7 in which the appropriate solvent is hexane, the reduced temperature is about 0° C. and the active base is potassium hexamethyldisilyazide.

9. A process according to claim 8 in which R¹ and R² are each propyl and n is 3.

10. A process according to claim 9 wherein the compound prepared is N,N-dimethyl-8,8-dipropyl-2-azaspiro[4.5]decane-2-propanamine-1-one.

11. A process according to claim 9 wherein the compound prepared is N,N-diethyl-8,8-dipropyl-2-azaspiro[4.5]decane-2-propanamine-1-one.

12. A process according to claim 9 wherein the compound prepared is 2-(3-piperidinopropyl)-8,8-dipropyl-2-azaspiro[4.5]decane-1-one.

13. A compound of the formula III

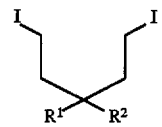

wherein R¹ and R² are as defined in claim 1.

14. A compound of the formula II

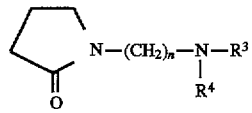

wherein R³ and R⁴ are as defined in claim 1.

* * * * *